(12) United States Patent
Driedger

(10) Patent No.: US 8,562,535 B2
(45) Date of Patent: Oct. 22, 2013

(54) PROBE HOLDER

(76) Inventor: Daniel Richard Driedger, Surrey (CA)

( * ) Notice: Subject to any disclaimer, the term of this patent is extended or adjusted under 35 U.S.C. 154(b) by 28 days.

(21) Appl. No.: 13/160,284

(22) Filed: Jun. 14, 2011

(65) Prior Publication Data

US 2012/0323125 A1    Dec. 20, 2012

(51) Int. Cl.
  *A61B 8/14* (2006.01)
  *A61B 1/00* (2006.01)

(52) U.S. Cl.
  USPC ............ 600/462; 600/102; 600/139; 600/459

(58) Field of Classification Search
  USPC ......... 600/101, 102, 121, 134, 139, 459, 462, 600/463
  See application file for complete search history.

(56) References Cited

U.S. PATENT DOCUMENTS

| | | | |
|---|---|---|---|
| 4,620,527 A | 11/1986 | Adams, Jr. | |
| 5,415,157 A | 5/1995 | Welcome | |
| 5,415,287 A | 5/1995 | Hamano et al. | |
| 5,558,841 A | 9/1996 | Nakagawa et al. | |
| 6,406,665 B1 | 6/2002 | Held | |
| 2006/0241476 A1* | 10/2006 | Loubser | 600/463 |

FOREIGN PATENT DOCUMENTS

| | | | |
|---|---|---|---|
| JP | 2000079125 A | | 3/2000 |
| JP | 2010137005 A | * | 6/2010 |

OTHER PUBLICATIONS

Robert F. Brooker, "Transesophageal Echocardiography Probe Holder", Anesth Analg 1994;79, p. 810.
Geneviève Côté et al, "Transesophageal echocardiography-related complications", Can J Anesth 55:9, Sep. 2008 p. 622.
Motoshi Kainuma et al, "A Convenient Holder of the Transesophageal Echocardiography Probe", Anesthesiology, 93:6, Dec. 2000, p. 1564.
Luis G. Michelsen, "A More Simple Holder for the Transesophageal Echocardiography Probe", Anesth Analg, 1998;86 p. 667.
L. Pineau et a, "Endoscope drying/storage cabinet: interest and efficacy", Journal of Hospital Infection (2008) 68, p. 59.
William A. Rutala et al, "Guideline for Disinfection and Sterilization in Healthcare Facilities", Department of Health and Human Services, 2008.
Bruce D. Spiess et al, "Transesophageal Echocardiography Probe Holder", Anesth Analg 1997;85 p. 945.
Jean Taillefer et al, "A comprehensive strategy to avoid transesophageal echocardiography probe damage", Can J Anesth 2002 / 49: 5 / p. 500.

* cited by examiner

*Primary Examiner* — Michael Rozanski
(74) *Attorney, Agent, or Firm* — Clark Wilson LLP

(57) ABSTRACT

A probe holder having a removable mechanical retention device; a first tube having a longitudinal slot and two opposing notches at each end, the notches configured for engaging the removable mechanical retention device; a second tube having a longitudinal slot and configured for rotational mating with the first tube; a top cap and a bottom cap, each of the top cap and bottom cap being configured for releasably engaging the first tube with the removable mechanical retention device, and for restraining rotation of the first tube when so engaged, while permitting rotation of the second tube relative to the first tube between an open configuration and a closed configuration.

36 Claims, 12 Drawing Sheets

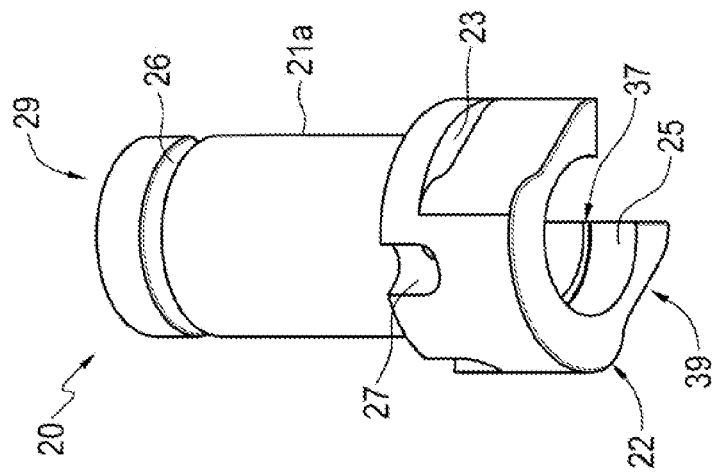
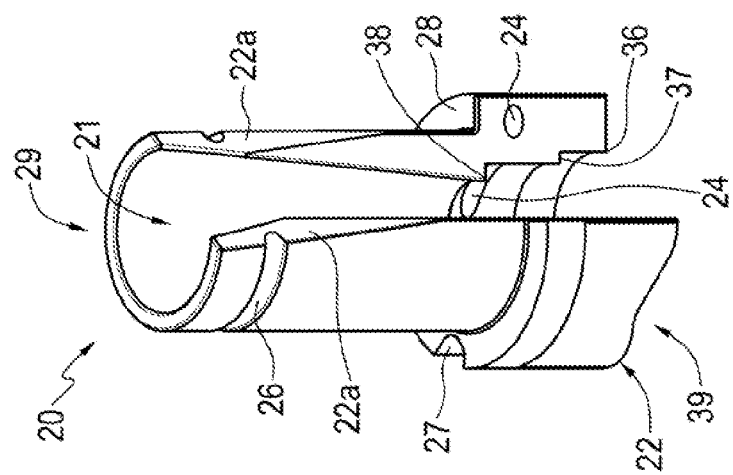
FIG. 3A
FIG. 3B

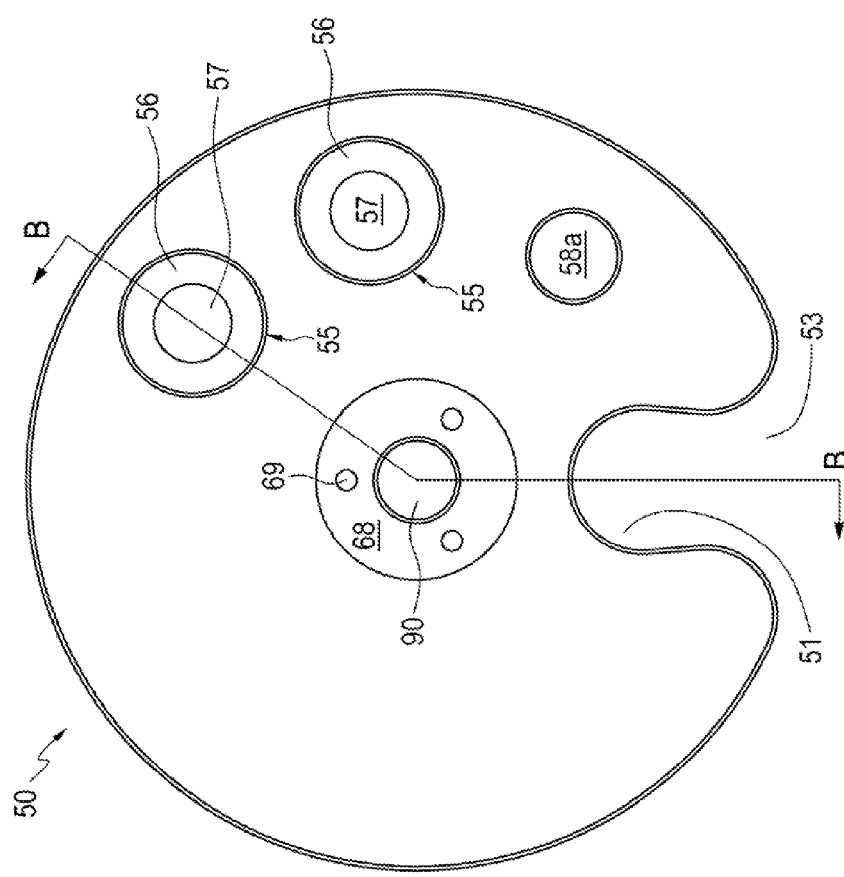

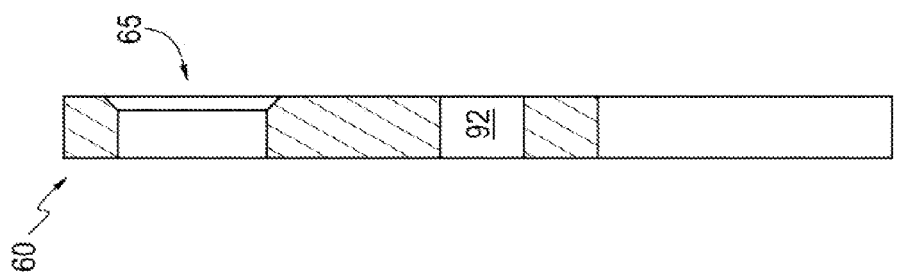
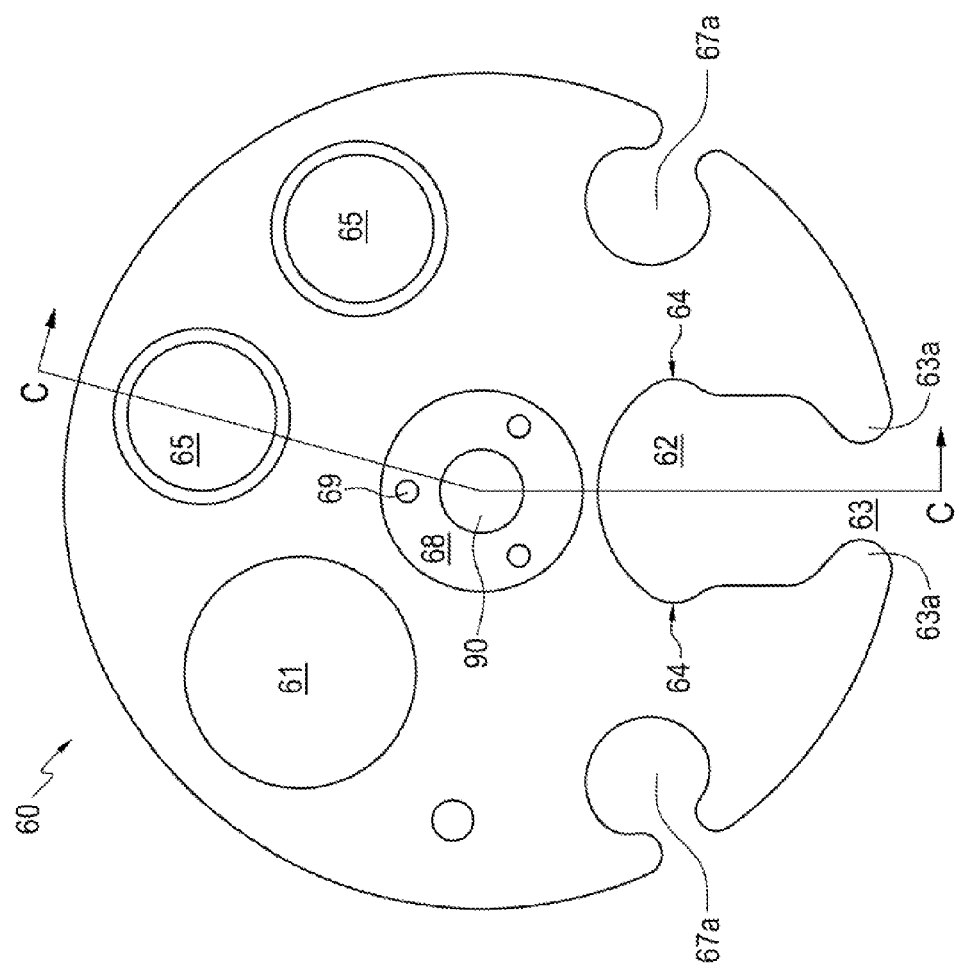
FIG. 7B
FIG. 7A

PROBE HOLDER

FIELD OF THE INVENTION

The present invention relates to an apparatus for holding and protecting a medical probe such as an endoscope or TEE probe.

BACKGROUND OF THE INVENTION

A variety of medical devices have been designed to enable access to the interior of the body for examination and/or treatment. Examples of such devices include endoscopes and flexible probes, such as transesophageal echocardiography (TEE) probes for accessing thoracic structures in a body.

Probes and endoscopes (collectively "probes") generally comprise an elongated flexible body with an articulable tip at a distal end, and a proximal end coupled to a probe handle, the handle configured to allow for manipulation of the device. The articulable tip at the distal end accommodates one or more transducer elements. In the case of a TEE probe, the distal end is introduced into a subject's esophagus to allow for ultrasound scanning of the subject's heart.

A variety of probes are known in the art, and a variety of features may be additionally incorporated into such devices to provide rotational functionalities, accommodate multiple transducer elements, multi-dimensional imaging and the like (e.g. U.S. Pat. Nos. 4,543,960, 5,351,691, 5,669,389, 5,156,155, 5,176,142, 5,413,107). U.S. Pat. No. 5,388,584 describes a shaft for a probe, configured for prevention of fluid intrusion.

Taillefer 2002 (Canadian Journal of Anesthesiology 49:500-502) describes a device for holding a TEE probe handle that can be manipulated by one hand of a user, and suggests that kinking of the probe shaft may be prevented by careful positioning. Storage of the probe using a tip protector and holder (the holders installed in the OR and/or storage and cleaning rooms) is also indicated. As addressed by Taillefer 2002, the operating room is a particularly risky site for damage to probes—they are one of many pieces of equipment surrounding the patient, and may be disconnected, reconnected, and handled by multiple staff during a procedure. As in any crowded workspace, mishandling and dropping may occur, causing damage to the probe, which are expensive to replace.

Several devices for aiding in holding or supporting probes in storage and/or use are described. Kainuma 2000 (Anesthesiology 93:1564), Spiess 1997 (Anesthesia and Analgesia 85:944), Michelsen 1998 (Anesthesia and Analgesia 86:677) and Brooker 1994 (Anesthesia and Analgesia 79:810) all describe various devices for holding a probe in a convenient position and/or location when in use, following use, or awaiting use. JP 2000079125 to Osada also describes a keeper for an ultrasonic diagnostic device (e.g. a TEE probe).

Apparatus and methods for cleaning of endoscopes are described in, for example, U.S. Pat. No. 5,558,841.

US Patent Publication 2006/0241476 describes an apparatus and method for holding a probe, a barrier system for infection control, and a liner for use therewith.

Pineau 2008 (J. Hosp Infect. 68:59-65) describes a drying and storage cabinet for endoscopes, and investigated the efficacy of air circulation on microbial contamination.

Other devices for holding or protecting endoscopes are described in U.S. Pat. Nos. 5,415,287, 4,620,527 and 5,415,157. U.S. Pat. No. 6,406,665 describes an apparatus and method for disinfection and electrical safety testing of probes.

What is needed is a probe holder that protects a probe from damage and contamination during storage and transportation, that provides convenient access during use, that resists contamination and that is well-suited to cleaning.

SUMMARY OF THE INVENTION

The present invention relates to a probe holder that addresses such needs.

In accordance with one aspect of the invention, there is provided a probe holder comprising a removable mechanical retention device; a first tube comprising a longitudinal slot and two opposing notches at each end of the first tube, the notches configured for engaging the removable mechanical retention device; a second tube comprising a longitudinal slot, and configured for rotational mating with the first tube; a top cap and a bottom cap, each of the top cap and bottom cap configured for releasably engaging the first tube with the removable mechanical retention device, and for restraining rotation of the first tube when so engaged, while permitting rotation of the second tube relative to the first tube between an open configuration and a closed configuration.

In some aspects of the invention, the components (top cap, bottom cap, first and second tubes, mechanical retention device and others) are of monolithic construction, and configured to minimize, or are without, non-separable joints. In some aspects of the invention, all surfaces of the components of the probe holder are accessible for cleaning and/or disinfecting. Some or all of the components of the probe holder may also be suitable for autoclaving or other sterilization methods.

In some aspects of the invention, suitable materials for use in various components of the probe holder have characteristics of low porosity, smooth surface, high temperature resistance, high chemical resistance, and are preferably machineable.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE DRAWINGS

These and other features of the invention will become more apparent from the following description in which reference is made to the appended drawings wherein:

FIG. 3A shows a perspective view of a top cap of the probe holder of FIG. 1, according to an embodiment of the invention.

FIG. 3B shows a second perspective view of the top cap of FIG. 3A, according to an embodiment of the invention.

FIG. 6A shows a top view of a lower support plate for a probe holder, according to an embodiment of the invention.

FIG. 6B shows a section view of the lower support plate of FIG. 6A along the line B-B, according to an embodiment of the invention.

FIG. 7A shows a top view of an upper support plate for a probe holder, according to an embodiment of the invention.

FIG. 7B shows a section view of the upper support plate of FIG. 7A along the line C-C, according to an embodiment of the invention.

DESCRIPTION OF THE INVENTION

The invention provides, in part, a holder for a probe. More particularly, the invention provides a probe holder having a first tube with a longitudinal slot and two opposing notches at each end, the notches configured for engaging a removable mechanical retention device; a second tube comprising a longitudinal slot, and configured for rotational mating with the first tube; and a top cap and a bottom cap. Each of the top cap and bottom cap are configured for releasably engaging the first tube with the removable mechanical retention device, and for restraining rotation of the first tube when so engaged, while permitting rotation of the second tube relative to the first tube between an open configuration and a closed configuration.

The term "probe" refers generally to any medical device having an extended portion for surgical or visual access to internal aspects of a body. The body may be a human body or animal body, the animal may be a mammal. Examples of probes that may be held by various embodiments of the invention include endoscopes, transesophageal echocardiography (TEE) probes, and the like.

Figure 1:
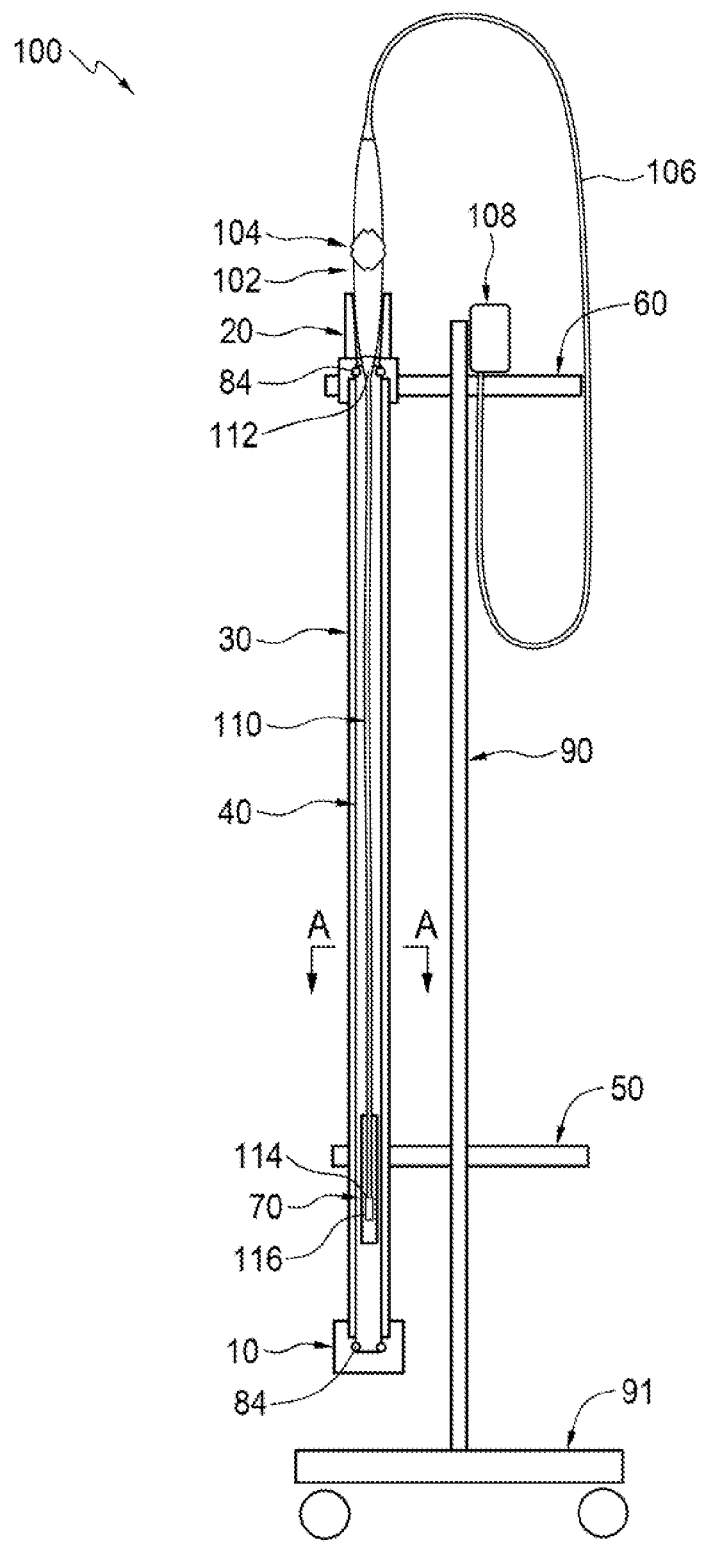
FIG. 1 shows a longitudinal section view of a probe holder, according to an embodiment of the invention.
Figure 1A:
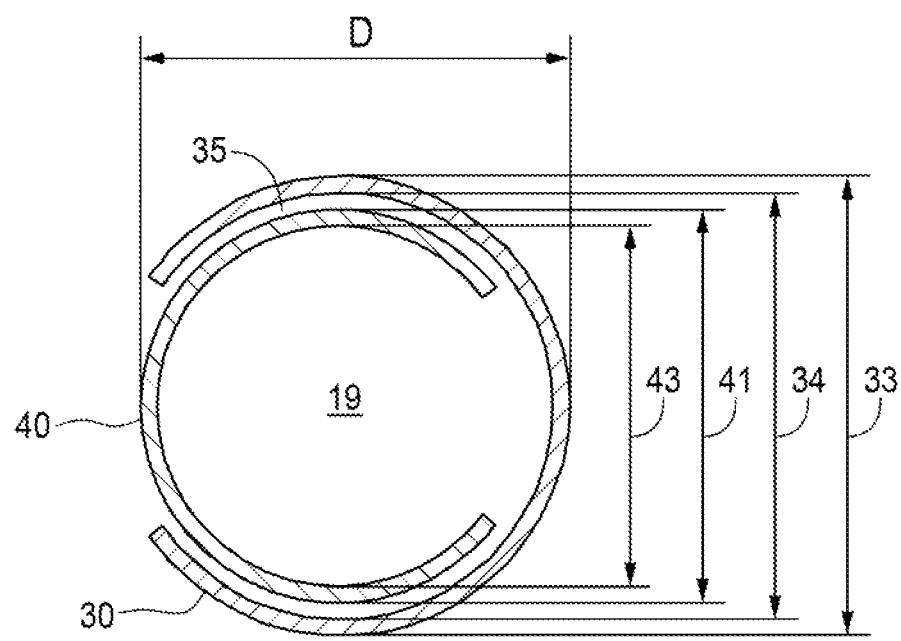
FIG. 1A shows a section view of the probe holder of FIG. 1 along the line A-A, according to an embodiment of the invention.
Figure 1B:
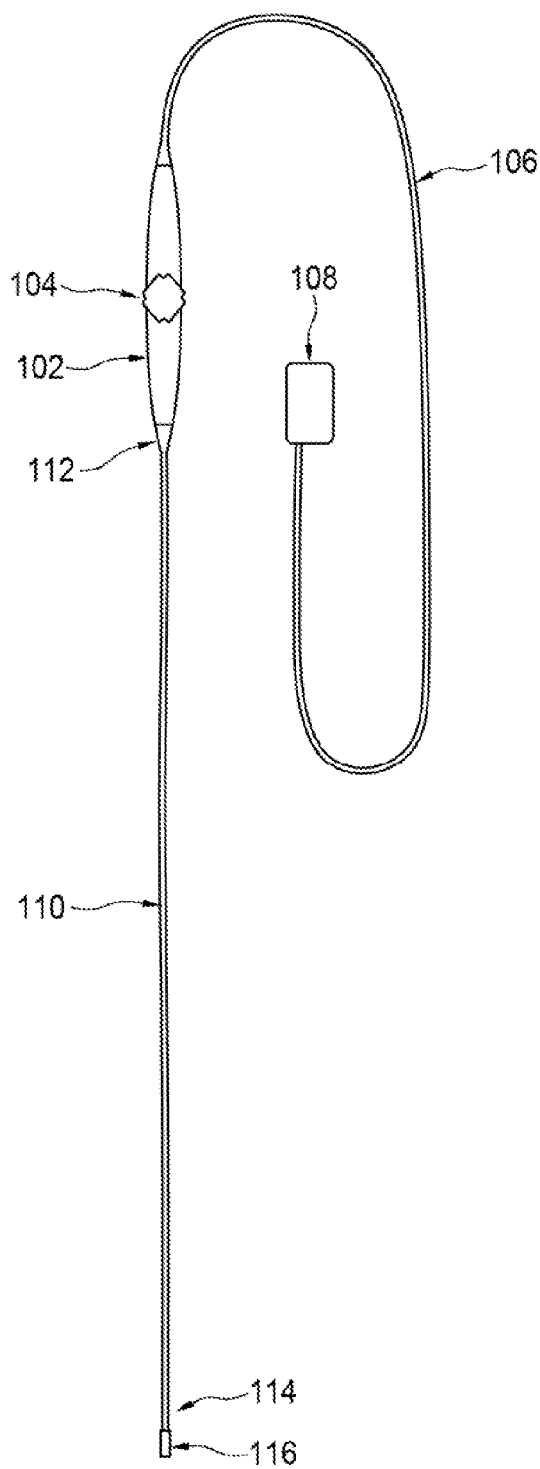
FIG. 1B shows a generic probe that may be used with a probe holder, according to various embodiments of the invention.
Figure 2A:
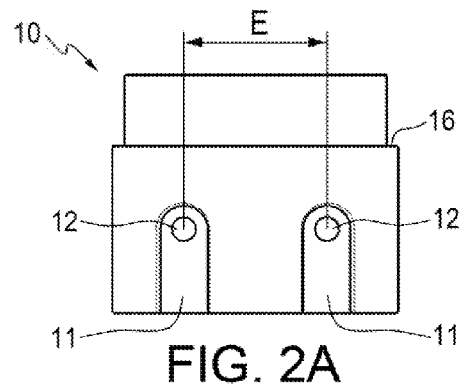
FIG. 2A shows a front view of a bottom cap of the probe holder of FIG. 1, according to an embodiment of the invention.
Figure 2B:
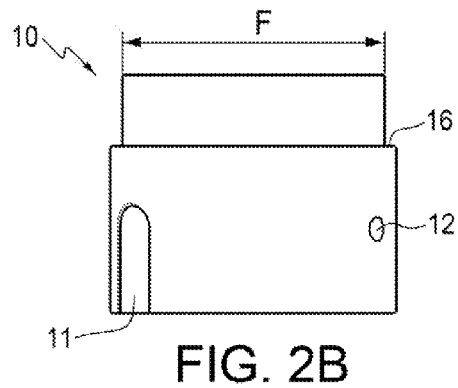
FIG. 2B shows a side view of the bottom cap of FIG. 2A, according to an embodiment of the invention.
Figure 2C:
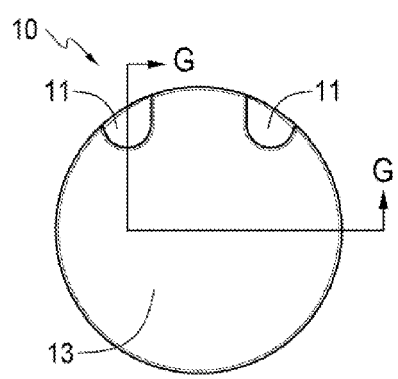
FIG. 2C shows a bottom view of the bottom cap of FIG. 2A, according to an embodiment of the invention.
Figure 2D:
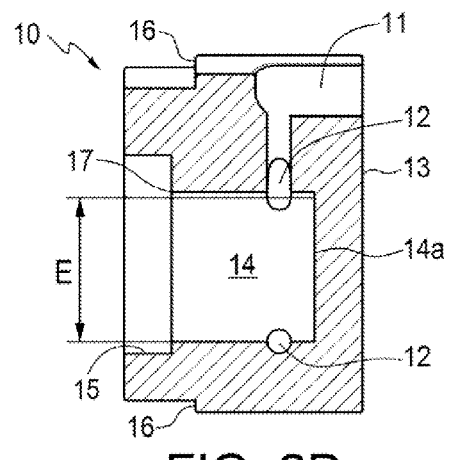
FIG. 2D shows a sectional view of the bottom cap of FIG. 2A, along the line G-G according to an embodiment of the invention.
Figure 2E:
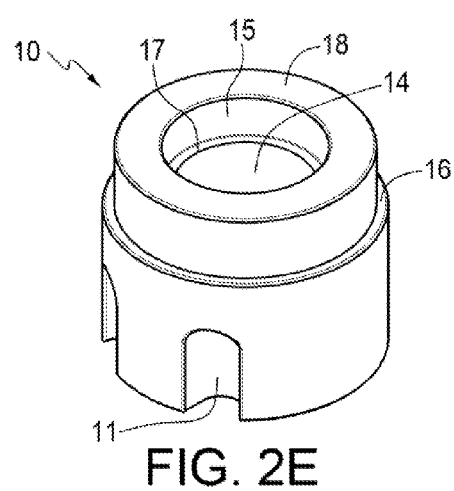
FIG. 2E shows a top perspective view of the bottom cap of FIG. 2A, according to an embodiment of the invention.
Figure 2F:
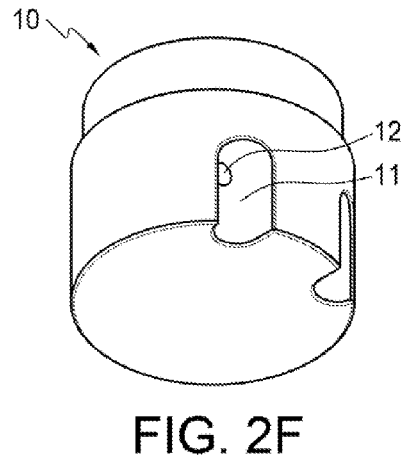
FIG. 2F shows a bottom perspective view of the bottom cap of FIG. 2A, according to an embodiment of the invention.
Figure 3C:
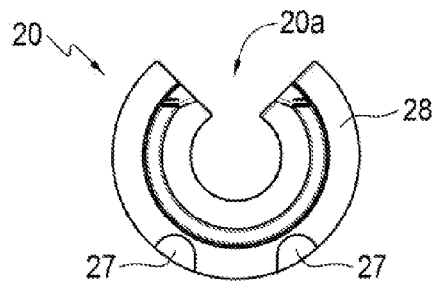
FIG. 3C shows a top view of the top cap of FIG. 3A, according to an embodiment of the invention.
Figure 3D:
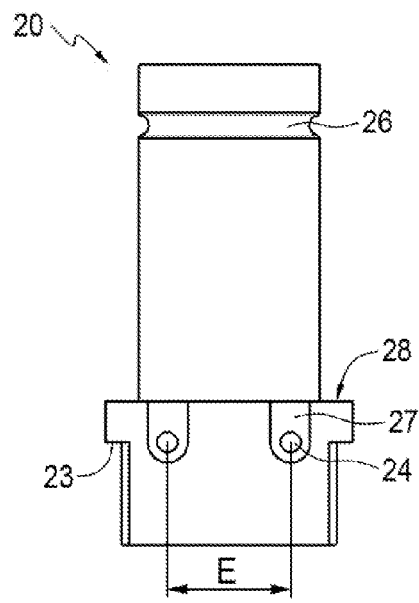
FIG. 3D shows a rear view of the top cap of FIG. 3A, according to an embodiment of the invention.
Figure 3F:
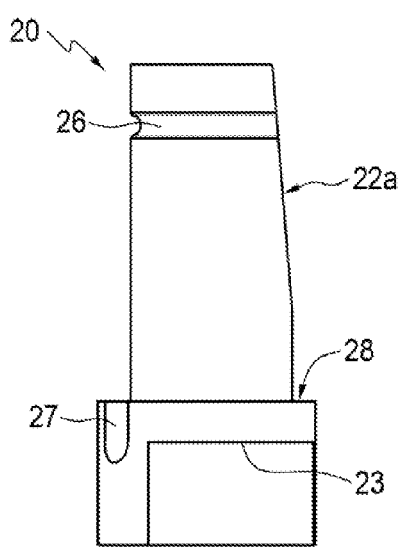
FIG. 3F shows a side view of the top cap of FIG. 3A, according to an embodiment of the invention.
Figure 3E:
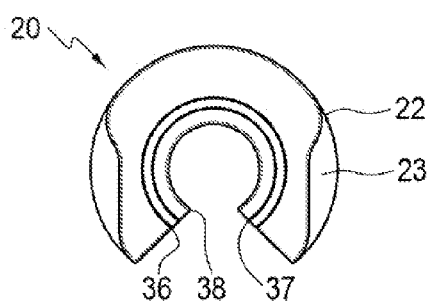
FIG. 3E shows a top view of the top cap of FIG. 3A, according to an embodiment of the invention.

FIG. 1B shows a generic illustration of a TEE probe—an example of a probe that may be held by a probe holder according to various embodiments of the present invention. The probe has a probe handle 102 with a controller 104, with a power cable 106 connecting the probe handle 102 to an electrical connector 108 for connection to a signal and power source, and an elongated probe section 110 having a proximal end 112 connected to the probe handle 102, and a distal end 114 with an articulable tip 116. The controller 104 may be a knob or equivalent guiding apparatus for guiding the direction of the distal end 114 as is known in the art, or may be other control devices, as are known in the art. The distal end 114 may house an ultrasound transducer, lens for visualization (coupled to fiber optic or other connections as are known in the art), or other functional components as are known in the art.

As probes are generally intended for use with multiple subjects (cleaned and disinfected between use) and used internally, cleanliness and careful handling is necessary to prevent nosocomial infection (e.g. from a damaged or improperly disinfected probe), and damage to the probe when being disinfected and used. Guidelines for handling, cleaning and disinfection of such probes exist, however their practice may not extend through the entire use-cycle of the device. The probe handle 102 may be heavy, and if not carefully put down when not in use, may fall on the floor and be damaged on impact. Even if the probe handle 102 is safely placed, the probe's length may leave the tip 116 resting on the floor, or prone to entanglement with equipment, wires and the like. While durable, these precision instruments are often unable to withstand dropping and mishandling. Examples of guidelines for handling, cleaning, disinfection and sterilization of medical equipment and devices are known in the art, and include, for example the Guideline for disinfection and Sterilization in healthcare Facilities, 2008 W. A. Rutala et al, (Healthcare Infection Control Practices Advisory Committee, a publication of the US Centre for Disease Control, Department of Health & Human Services).

The invention provides, in part, a holder for an elongated probe, such as a TEE probe or endoscope. The holder is constructed so that all components have smooth surfaces and are monolithic in construction, and joints that are not separable (e.g. welds, press-fit, screws, bolts or the like) are avoided. Thus, contaminant capture points are minimized, or in some embodiments eliminated. A "contaminant capture point" refers generally to a joint, crevice or other confined or difficult to access space where dust, grit or contaminating matter may accumulate and be difficult or impossible to remove. Contaminating matter may include body fluids or particulates, microbial contamination or other material that a probe may be exposed to in the course of use in an operating room, procedure room, cleaning location, storage space or the like. All surfaces of the probe holder may be accessed for cleaning manually, or using automated cleaning equipment or a combination thereof.

Suitable materials for use in various components of the probe holder have characteristics of low porosity, smooth surface, high temperature resistance (e.g. above about 50° C., and may be as high as about 140° C.), high chemical resistance (e.g. not damaged by cleaning or disinfecting agents under conditions of use), and are preferably machineable. Examples of such materials include, without limitation, steel, stainless steel, aluminum, coated aluminum, anodized aluminum, titanium, alloys thereof, various plastics including polyoxymethylene, and the like.

Referring to FIG. 1, a probe holder according to one embodiment of the invention is shown generally at 100. The probe holder 100 comprises a first (inner) tube 40 and a second (outer) tube 30. Each of the inner tube 40 and outer tube 30 is of a length sufficient to accommodate a flexible section of a probe placed therein, the inner tube 40 being slightly longer than the outer tube 30 to accommodate reversible fixation in a bottom cap 10 and a top cap 20 by a mechanical retention device (e.g. "clip") 80 when the probe holder 100 is assembled. In some embodiments, the elongated probe, including the distal tip 116 of the probe is suspended within an interior space of the holder (e.g. without resting on or contacting the bottom cap 10, addressed below) when the probe holder 100 is assembled and a probe placed therein.

Figure 4:
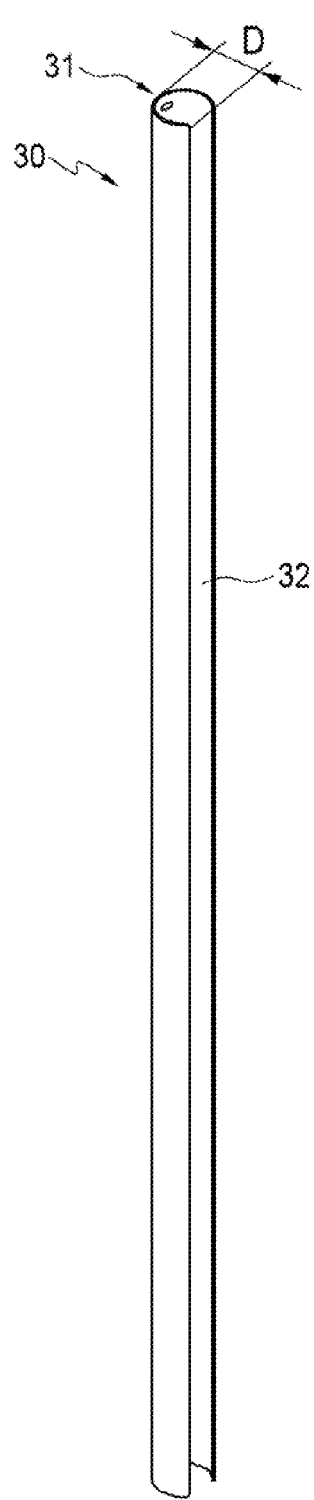
FIG. 4 shows a perspective view of an outer tube member of the probe holder of FIG. 1, according to an embodiment of the invention.
Figure 5:
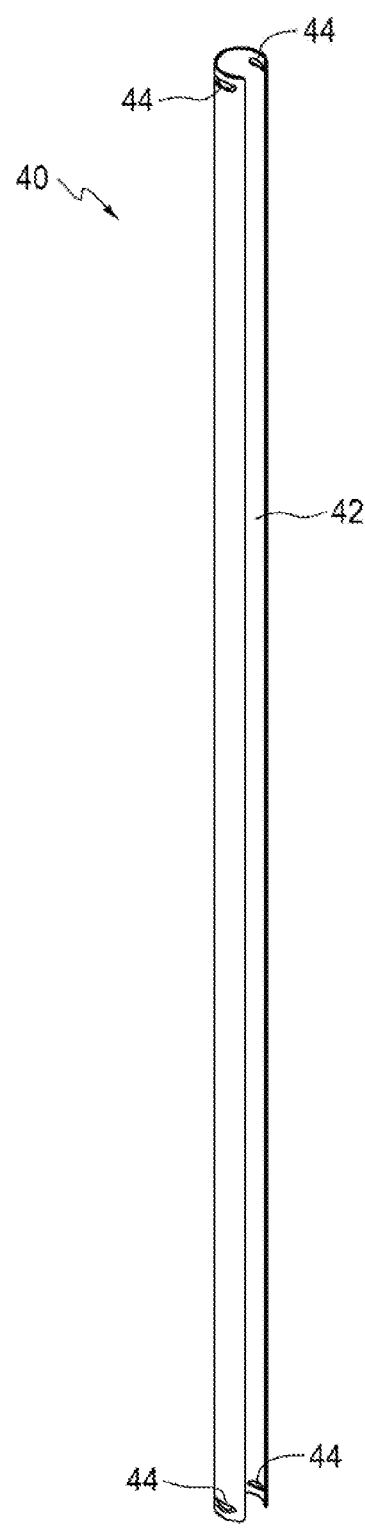
FIG. 5 shows a perspective view of an inner tube member of the probe holder of FIG. 1, according to an embodiment of the invention.

The inner tube 40 and outer tube 30 have a C-shaped cross-section, each with a respective longitudinal slot 42, 32 as shown in FIGS. 4 and 5, extending the length of the tube 40, 30. The outer tube 30 has a dimension D (FIGS. 1A, 4), which is less than the outer diameter 33 of the outer tube 30, to facilitate placement or removal of the assembled probe holder 100 on support plates 50, 60, addressed below. Dimension D may be greater than the outer diameter of the inner tube 40. The longitudinal slots 32, 42 are the same, or substantially the same width and sufficient to allow for ingress and egress of the probe when the probe holder 100 is assembled.

The inner tube 40 and outer tube 30 are mated by placement of the inner tube 40 into a lumen of outer tube 30 as shown in FIG. 1A. Rotation of the inner tube 40 or outer tube 30 aligns the longitudinal slots 42, 32 and allows for insertion or removal of an elongated section of a probe within a lumen of inner tube 40. When mated, the inner diameter 34 of the outer tube 30 and the outer diameter 41 of the inner tube 40 yield a gap 35 therebetween, the gap 35 extending the length of the overlap of the inner tube 40 and the outer tube 30. The gap 35, when the slots 32, 42 are in opposite position from each other, may facilitate circulation of air and prevent condensation of fluid on the probe, or allow for fluid that may be on the probe to evaporate following use, cleaning and/or disinfection of the probe (e.g. air drying), while the probe remains isolated by the probe holder 100, with the tubes 30, 40 in a closed configuration, from external contact or contamination (for example from dust) when in transport or storage.

In some embodiments, the tubes 30, 40 are nested together, concentric and/or coaxial. The outer tube 30 substantially circumscribes the inner tube 40. The inner tube 40 substantially inscribes the outer tube 30. The shape and size of each tube 30, 40 and the relationships between them may be selected and adjusted to encourage such nesting and respective rotation for aligning and disaligning the respective longitudinal slots 32, 42.

Figure 10:
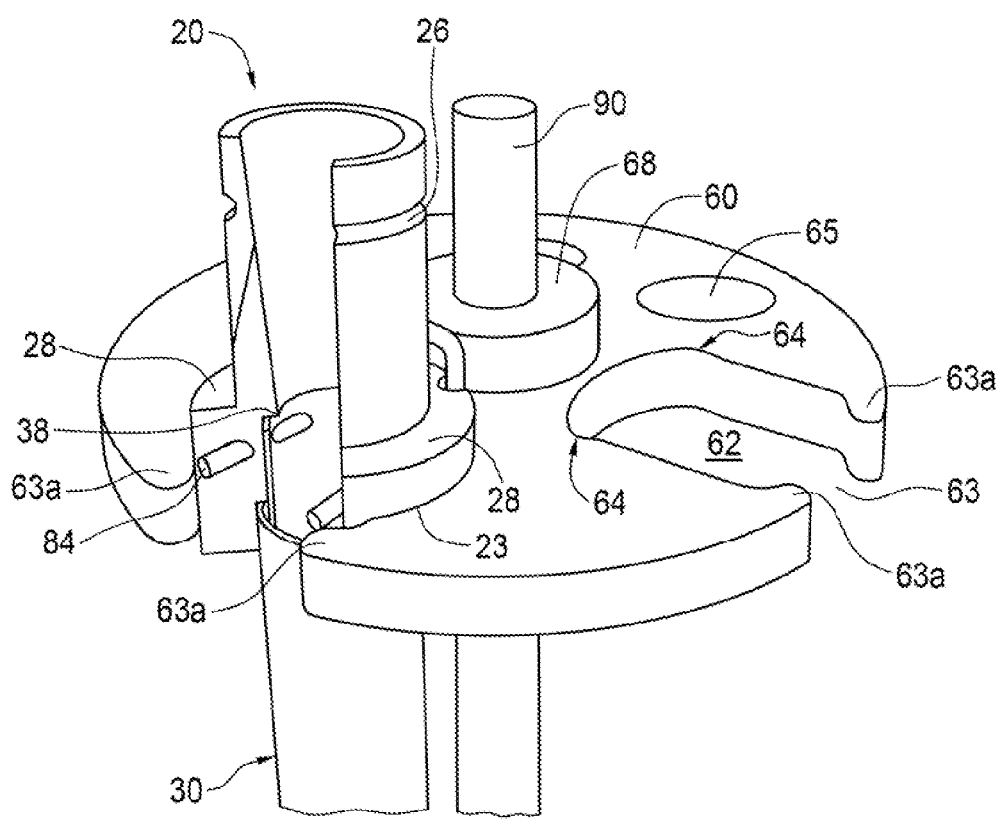
FIG. 10 shows a magnified perspective view of the upper support plate of FIG. 1, according to one embodiment of the invention.
Figure 10A:
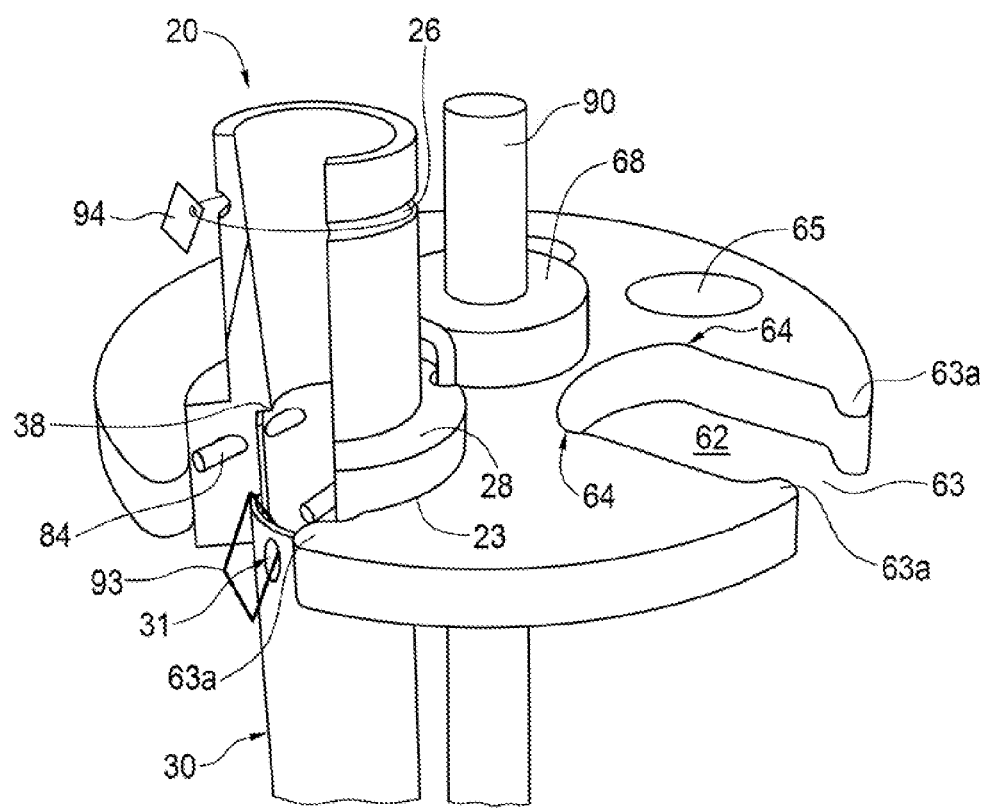
FIG. 10A shows the magnified perspective view of FIG. 10, with status markers at the circumferential groove of the top cap and the tag hole of the outer tube, according to various embodiments of the invention.

FIGS. 1A, 10A illustrate a 'closed' configuration of the probe holder, where the outer tube 30 is rotated so that the longitudinal slots 32, 42 are not overlapping or aligned to provide access to an interior space 19 of the probe holder 100. An open configuration (not shown) has the outer tube 30 rotated relative to the inner tube 40 so that the longitudinal slots 32, 42 are aligned, and the interior space 19 of the probe holder 100 is accessible therethrough. In some embodiments, the open configuration provides for the longitudinal slots 32, 42 to be aligned with a cut-away section 20a of the top cap 20, addressed below.

The inner tube 40 has notches 44 on opposing sides and at both ends, to accommodate tines 84 of the mechanical retention device (e.g. "clip") 80 when the probe holder 100 is assembled. The ends of the inner tube 40 are equivalent and identically configured so as to mate with either of the bottom cap 10 or the top cap 20. The outer tube 30 optionally has a tag hole 31 at each end, that serves as a 'closed' position indicator when it is obviated in the top cap 20 opening 20a by rotation of the outer tube 30 and also to accommodate an optional status marker 93, as shown in FIG. 10A. Note that the tag hole 31 is visible only at one end of the outer tube 30 as illustrated in FIG. 4; however, it will be appreciated that an identical tag hole 31 (not shown) may be found at the other end of the outer tube 30. The hole 31 is present at each end of the outer tube 30 to allow for non-specific assembly of the outer tube 30 into the top cap 20 and the bottom cap 10.

In some embodiments the hole at the bottom end of the outer tube 30 is masked by a recess 14 in the bottom cap 10 to limit circulation of air through this bottom hole into the inner tube 40 lumen when the holder is assembled. Similar to the inner tube 40, the ends of outer tube 30 are equivalent and identically configured so as to mate with either of the bottom cap 10 or the top cap 20. Examples of optional status markers 93 include tags or labels applied following cleaning of the probe, such as a pull thru tag or seal, padlock tag or seal, or similar tamper-evident closure as are known in the art. One example is illustrated in U.S. Pat. No. 4,968,075, others will be apparent to those skilled in the art.

FIGS. 2A-2E show views of a first (base or bottom) cap 10. The bottom cap 10 has a closed exterior 13 and a centre recess 14, the centre recess 14 is of a diameter to provide a friction fit with an end of the inner tube 40. The end of the inner tube 40 rests on a blind end (closed end) 14a of the centre recess 14. The blind end 14a may preventingress of a contaminant, or egress of fluids (e.g. body fluid that may drip from a used probe) as the probe is being stored or transported in the probe holder. The bottom cap 10 further includes parallel holes 12 that extend through the bottom cap 10 and are spaced apart distance E (measured centre to centre of holes 12); distance E of the bottom cap 10 (and counterpart top cap 20, addressed below) corresponds to the outer diameter 41 of inner tube 40. Notches 44 of the inner tube 40 intersect with parallel holes 12 when aligned, and are engaged by tines 84 of the clip 80 to secure the bottom cap 10 to the inner tube 40.

A first rotation guide 15 is bounded by an internal circumferential lip 17 above the blind end 14a of the centre recess 14, and a top surface 18. An end of the outer tube 30 rests on the internal circumferential lip 17, and is supported by the first rotation guide 15 when the probe holder 100 is assembled. The first rotation guide 15 facilitates rotation of the outer tube 30 relative to the inner tube 40, to align the longitudinal slots 32, 42 to facilitate placement and removal of the probe in the probe holder 100. The internal diameter of the first rotation guide 15 is selected to provide an interference fit for the end of the outer tube 30, to provide friction requiring purposeful action to rotate the outer tube 30.

Dimension F of the bottom cap 10 is substantially the same as the diameter of a hole 61 in an upper support plate 60 (addressed below) to facilitate placement and retention of the bottom cap 10, when the probe holder 100 is in a disassembled state for cleaning. An external circumferential lip 16 retains the bottom cap 10 on the upper support plate 60 when in a disassembled state.

The tines 84 of the clip 80 may be separate straight members, or may be joined to form a single piece. In some embodiments the single piece may be U-shaped, such as a U-shaped clip where the tines 84 are connected by a connector 82, forming the bottom of the "U". The ends 86 of the tines 84 may be blunt, chamfered or rounded, or similar shape to facilitate insertion into the holes 12 (and holes 24 in the top cap 20, addressed below) and avoid contaminant capture points. In some embodiments, the clip 80 may be a bent U-shape, such as the embodiment illustrated in FIGS. 9A-9D, where a perpendicular side 85 of the clip 80 is illustrated.

The holes 12, notches 44 and (optional) recesses 11 in the bottom cap 10 interact to provide substantially parallel channels through the bottom cap 10 and the inner tube 40. When the clip 80 is inserted in the holes 12 of the bottom cap 10 and engages the notches 44 of the inner tube 40, the clip 80 is retained in the bottom cap 10 by an interference fit.

The interference fit may result from an angle α ("alpha") between the tines 84 of the clip 80, the diameter of the tines 84, or in combination the angle α between the tines and the diameter of the tines. In some embodiments, the tines 84 may be parallel (i.e. the angle alpha may be zero, or about zero). In some embodiments, the tines 84 may be angled outwards in the same plane, and the angle alpha may be from about zero to about 10 degrees, or any amount therebetween, for example 1, 2, 3, 4, 5, 6, 7, 8, 9, 10, or any amount therebetween. In some embodiments, the tines 84 may be angled towards each other in the same plane and the angle alpha may be from about zero to about 10 degrees, or any amount therebetween, for example 1, 2, 3, 4, 5, 6, 7, 8, 9, 10, or any amount therebetween. In some embodiments, the tines 84 are angled outwards, in the same plane, such that the angle alpha is between about 1 degree to about 5 degrees. Insertion of the clip 80 into the parallel holes 12 and notches 44 of the inner tube 40 is facilitated by manual compression of the tines 84 when inserting into the parallel holes 12.

Choice of material for the clip 80 may influence selection of the angle alpha. For example, a more rigid material may accommodate a lesser angle alpha, while a more flexible material may be suitable for use with a greater angle alpha. Selection of suitable material for the clip 80 will be within the ability of one skilled in the art. Examples of such materials includes, without limitation, steel, stainless steel, aluminum, coated aluminum, anodized aluminum, various plastics including polyoxymethylene (e.g. Delrin™) or the like.

FIGS. 3A-3F show views of a second (top) cap 20. The top cap 20 is generally cylindrical with a cut-away section (e.g. at 20a of FIG. 3C) to facilitate placement and removal of the probe, and is configured to receive the inner tube 40 and the outer tube 30, and a clip 80 in a manner similar to that for the bottom cap 10.

The top cap 20 has a lower edge 36 at a second (lower) end 39 and a first circumferential lip 37 for accommodating an end of the outer tube 30, the lower edge 36 and first circumferential lip 37 bounding a second rotation guide 25. A second circumferential lip 38 accommodates an end of the slightly longer inner tube 40. The top cap 20 further includes parallel holes 24 extending through the top cap 20 and spaced apart distance E. As discussed above, distance E of the top cap 20 corresponds to the outer diameter 41 of the inner tube 40. The notches 44 of the inner tube 40 intersect with the parallel holes 24 in the top cap 20 when aligned, and are engaged by the clip 80 in a similar manner as was described above for the bottom cap 10. A sectional view of one of the holes 24 is provided in FIG. 3A, showing an elliptical cutaway of the one of the holes 24, which aligns with one of the notches 44 and is engaged by one of the tines 84.

In a manner similar to that of the bottom cap 10, the second rotation guide 25 facilitates rotation of the outer tube 30 relative to the inner tube 40 to align the longitudinal slots 32, 42 to facilitate placement and removal of the probe in the probe holder 100. The internal diameter of the second rotation guide 25 is substantially the same as the internal diameter of the first rotation guide 15, and is selected to provide an interference fit for the end of the outer tube 30, to provide friction requiring purposeful action to rotate the outer tube 30.

By having the configuration of the parallel holes 12, 24, notches 44 of the inner tube 40, outer tube 30, and clip 80 identical for both top cap 20 and bottom cap 10, the orientation of the inner tube 40 and outer tube 30 is neutral (e.g. no 'top' or 'bottom' end independent of the assembled probe holder), and facilitates assembly by a user, as matching of particularly designed mechanical retention devices 80 with particular ends of the inner tube 40 and outer tube 30, and/or specifically the bottom cap 10 or top cap 20 is avoided. While the top cap 20 and bottom cap 10 are different, they mate equally well with either end of the mated inner tube 40 and outer tube 30 and are held with the same mechanical retention device 80 configuration.

The top cap 20 further includes an interior surface 21 that defines an interior space for receiving a probe. The diameter of the interior space is sufficient to accommodate a portion of the probe handle 102. In the embodiment illustrated in FIG. 3A, the interior surface 21 is angled inward from the first (top) end 29 of the top cap 20 to the second (lower) end 39 of the top cap 20, defining a tapered space. A neck 21a may be longer or shorter as desired to accommodate the size of the probe handle 102. An optional circumferential groove 26 on the top cap 20 accommodates an optional status marker 94 or similar tag, as described above. Depending on the specific configuration of the probe handle 102, placement of the status marker 94 may prevent inadvertent dislodging or removal of the probe—removal of the probe may thus require breaking of the tag.

In some embodiments, the top cap 20 and/or the interior surface 21 of the top cap 20 may have one or more recesses to accommodate a probe handle 102 with one or more buttons, knobs or other protuberances (not shown), for example the controller 104. In some embodiments, the cut-away section 20a of the top cap 20 may have a further, substantially vertical wedge removed, creating surfaces 22a (FIG. 3A) to accommodate various configurations of a probe handle 102 (e.g. one or more buttons, knobs or other protuberances, such as the controller 104), and may allow deeper seating of the probe handle 102 within the interior space of the top cap 20, or extension of the length of the neck 21a of the top cap 20, thereby providing for a more secure hold of the probe handle 102. Positioning of the circumferential groove 26 near the first (top) end 29 of the top cap 20 may allow the status marker 94 or similar tag to be positioned around the probe handle 102 and above a button, knob or other protuberance on the probe handle 102 (for example the controller 104), thereby preventing removal of the probe handle 102 when the status marker 94 is in place unless the status marker 94 is broken or removed.

Respective recesses 11, 27 in the bottom cap 10 and top cap 20 accommodate a connector 82 of the clip 80. The recesses 11, 27 may be of sufficient depth to accommodate the diameter of the connector 82 of clip 80, so that a perpendicular side 85 of the clip 80 is flush, or substantially flush, with the external surface of the cap 10, 20. This arrangement may serve to minimize protrusion of the clip 80 when in place, and may, in part, prevent inadvertent dislodgement of the clip 80.

Figure 8:
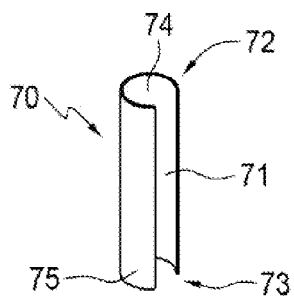
FIG. 8 shows a perspective view of a probe tip protector for the probe holder of FIG. 1, according to one embodiment of the invention.
Figure 9A:
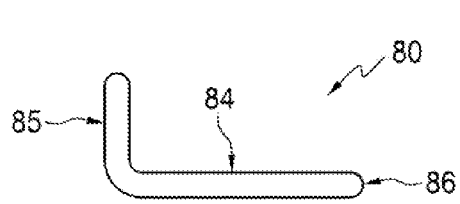
FIG. 9A shows a side view of a mechanical retention device for the probe holder of FIG. 1, according to one embodiment of the invention.
Figure 9B:
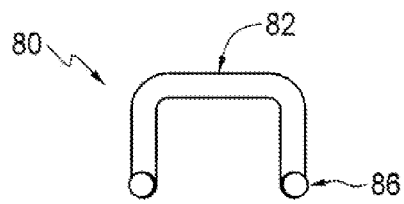
FIG. 9B shows an end view of the mechanical retention device of FIG. 9A, according to one embodiment of the invention.
Figure 9C:
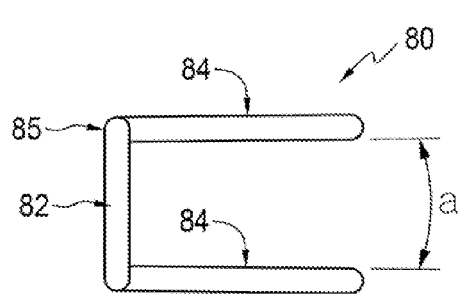
FIG. 9C shows a top view of the mechanical retention device of FIG. 9A and illustrating an angle α ("alpha"), according to one embodiment of the invention.
Figure 9D:
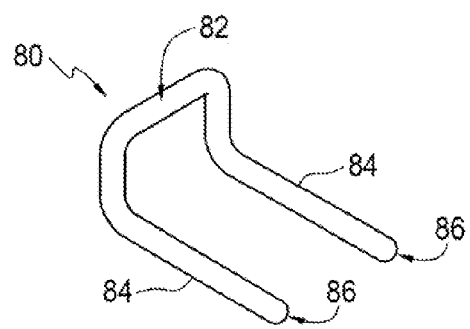
FIG. 9D shows a perspective view of the mechanical retention device of FIG. 9A, according to one embodiment of the invention.

For embodiments where a bent U-shaped clip 80 is employed, such as that illustrated in FIGS. 8, 10 and 10A, the connector 82 may extend beyond a shoulder 28 of the top cap 20, or the closed exterior 13 of the bottom cap 10. Such a configuration may further facilitate ease of manual removal of the clip 80 by applying pressure to connector 82, perpendicular to the longitudinal axis of the probe holder 100.

In some embodiments, the probe holder 100 may further comprise a tip protector 70 removably housed within the inner tube 40 (FIGS. 1, 8). The tip protector 70 is a tube with an interior surface 74, exterior surface 75, first end 72 and second end 73 and a longitudinal slit 71. The tip protector 70 may be of lesser length than inner tube 40 and movably positioned therein to surround the distal tip 116 of the probe held by the probe holder 100. The outer diameter of the tip protector 70 is slightly greater than the inner diameter 43 of the inner tube 40. The longitudinal slit 71 permits radial compression (e.g. manual) of the tip protector 70 to facilitate insertion and positioning into the inner tube 40. Release of radial compression permits retention of the tip protector 70 at a desired position within the inner tube 40 by spring tension, allowing for an interference fit of the tip protector 70 within the inner tube 40. The dimension of the longitudinal slit 71 may be selected to be sufficiently wide to permit compression for insertion of the tip protector 70 into the inner tube 40, but narrower than the width of the tip 116 of the probe to prevent the tip 116 of the probe from extending beyond the confine of the probe holder 100 (e.g. a probe with a degree of curve or curl may extend the tip 116 outside the probe holder 100, where it may be subjected to impact with other equipment, or persons). In some embodiments, the tip protector 70 may be made of a material more flexible or softer than that of the inner tube 40 and outer tube 30; use of a softer and/or more flexible material may provide additional protection ('cushioning') of the distal tip 116 from impact with the inner tube 40 when the probe holder 100 and probe are transported.

The interior surface 74 of the tip protector 70 may be of a constant internal diameter, or may be tapered towards one end (unidirectional taper), for example tapering from the first end 72 to the second end 73, with the first end 72 positioned closer to the top cap 20 of the assembled probe holder 100. In another embodiment, the interior surface 74 of the tip protector 70 is tapered axially from both the first end 72 and the second end 73 towards the centre of the tip protector 70 (bi-directional taper). In another embodiment the interior surface 74 may have a textured surface to provide compliant support of a distal tip 116 of the probe. A textured surface may include knobs, fingers, ridges, troughs, dimples, treads, hatching, embossments, protuberances or the like, and may be made of the same material, or different material as the tip protector 70. In some embodiments, the textured surface includes silicone.

In some embodiments, some edges of the various components of the probe holder 100 may be rounded or chamfered. Such rounded or chamfered edges may facilitate easier assembly of the probe holder, facilitate manufacturing, or offer improved safety to probe integrity and staff during handling or ease of cleaning.

Assembly of the Probe Holder and Support Device

To assemble the probe holder 100, the inner tube 40 is placed within the outer tube 30 as described above. If desired, the tip protector 70 is positioned in the inner tube 40. The bottom cap 10 is applied, placing an end of the inner tube 40 in the centre recess 14, and an end of the outer tube 30 on the internal circumferential lip 17. The bottom cap 10 is rotated relative to the inner tube 40 to align the holes 12 with the notches 44, and the clip 80 is applied as described above. The top cap 20 may be applied in a similar manner. The top cap 20 is placed on an opposite end of the mated inner tube 40 and outer tube 30, and rotated relative to the inner tube 40 to align the holes 24 with the notches 44, and the clip 80 is applied as described above. The assembled probe holder 100 may then be placed on a support to facilitate insertion of a probe.

To insert a probe, the outer tube 30 of the probe holder 100 is rotated with respect to the inner tube 40 to align their respective longitudinal slots 32, 42 to allow for access to the interior space 19 of the probe holder 100. The distal end 114 of the probe is placed in the upper end 74 of the tip protector 70 (if present) and the probe handle 102 placed in the interior space of the top cap 20 as bounded by the interior surface 21, guiding the remainder of the probe to lie within the interior (lumen) of the inner tube 40 of the probe holder 100. Where the optional tip protector 70 is tapered, as the probe tip 116 is inserted into the tip protector 70 as the probe is placed in the probe holder 100, the tip 116 is guided into a space of decreasing diameter to further restrain movement of the tip 116 within the probe holder 100.

A status marker 94 may optionally be applied to the circumferential groove of the top cap 20, surrounding the top cap 20 and probe in the probe holder 100 and preventing inadvertent removal or dislodging of the probe. In an embodiment where the outer tube 30 is provided with a tag hole 31, the status marker 94 may optionally be applied through the tag hole 31 when the outer tube 30 is rotated and positioned to cover the longitudinal slot 42 of the inner tube 40. Such a status marker 94 may prevent opening of the probe holder 100 unless the status marker 94 is broken or removed, thus preventing inadvertent removal or dislodging of the probe, and an indicator of a clean and unused status of the probe therein (when the status marker 94 is intact).

When assembled, the probe holder 100 is optimally configured for vertical, or substantially vertical support of a probe, including an endoscope, allowing the elongated probe section 110 to extend vertically. For probes or endoscopes with internal lumen(s), the vertical support configuration may allow for drainage of any liquid that may be within the lumen(s) following use or cleaning.

The assembled probe holder 100 (with or without a probe) may be placed in a support device for storage and/or transport. The support device may be configured for support of the probe holder 100 in a vertical, or substantially vertical, configuration. An embodiment of a support device with probe holder 100 is shown, at least in part, in FIG. 1. An exemplary support device may be mobile, and comprise a first (upper) support plate 60, a second (lower) support plate 50, a vertical support (pole) 90 and a wheeled base 91 as shown. Other examples of support devices may include an upper support plate 60 (and optionally lower support plate 50) affixed to a cabinet or wall, or other fixed location. In some embodiments, a support device may comprise a first support plate 60, the first support plate 60 affixed to a wall, shelf, pole or other support or equipment, for example, and a probe holder 100 according to various embodiments of the invention supported therewith, as described.

Advantages of a mobile support device include facilitation of transport of clean (unused) or used probes protected in a probe holder 100, avoiding transport on a generic trolley or other conveyance device where the probe may fall, or the probe or probe tip 116 be exposed to ambient air and dirt, and inadvertent contact with substances, equipment or persons, thus avoiding damage or contamination.

One embodiment of the upper support plate 60 is shown in FIG. 7A, with a sectional view along C-C shown in FIG. 7B. The upper support plate 60 has a central mounting portion, for example including a first cylindrical block 68, a second cylindrical block opposite the first cylindrical block (not shown) a hole 92 in the upper support plate 60 to accommodate a pole 90, and fasteners 69 to fix the upper support plate 60 to the pole 90. Exemplary fasteners include bolts, rivets, screws, nails, pegs or the like; the fasteners may be removable or non-removable.

The upper support plate 60 has a first grip 62 to receive the top cap 20 of the probe holder 100. FIG. 10 shows a portion of the probe holder 100 (top cap 20) engaged by the upper support plate 60. In some embodiments, the upper support plate 60 may have more grips than the first grip 62, so as to accommodate more than one probe holder 100.

A lead-in 63 of the first grip 62 has a width less than the outer diameter 33 of the outer tube 30, and greater than dimension D, to facilitate a 'rotate and load" action when placing or removing the assembled probe holder 100, and to prevent inadvertent dislodging of the probe holder 100 once placed on the support device.

An embodiment of a lower support plate 50 is shown in FIG. 6A, with a sectional view along B-B shown in FIG. 6B. The lower support plate 50 may be configured similarly to the upper support plate 60 for fixing to the pole 90 as described. The lower support plate 50 has a second grip 51 for receiving a lower portion of the probe holder 100, some distance above the bottom cap 10 as illustrated in FIG. 1. The second grip 51 may be of a diameter similar to (or slightly larger than) that of the outer diameter of the outer tube 30. In some embodiments, a lead-in 53 of the second grip 51 may have a restricted throat of a width less than the outer diameter 33 of the 30 outer tube, and greater than dimension D, again to prevent inadvertent dislodging unless the probe holder 100 is rotated to pass in a narrower orientation. The diameter of the second grip 51 is sufficient to restrain the assembled probe holder 100 without additional fasteners, but still permit rotation of the outer tube 30 between open and closed configurations by a user.

To install the probe holder 100 to the upper support plate 60, a user may employ a "rotate and load" action. The probe holder 100 is rotated to present a narrower dimension (e.g. dimension D) to the lead-in 63 and the probe holder 100 is inserted into the first grip 62, and rotated again to engage the index recesses 64 in the first grip 62 with the index tabs 22 of the top cap 20, thereby orienting the probe holder 100 for insertion/removal of the probe when the outer tube 30 is rotated to align the longitudinal slots 32, 42 of the respective outer tube 30 and inner tube 40. When the top cap 20 of the probe holder 100 is installed to the upper support plate 60, the index tabs 22 engage corresponding index recesses 64 in first grip 62 orienting the probe holder 100 for access with the longitudinal slots 32, 42 and the cutaway section 20a of the top cap 20 facing out (e.g. as illustrated in FIGS. 10, 10A), when the probe holder 100 is in an open configuration with the longitudinal slots 32, 42 aligned, or substantially aligned, with that of cutaway section 20a.

The shoulders 23 of the top cap 20 support the assembled probe holder 100 on the upper support plate 60. A perspective view of the top cap 20 of the assembled probe holder 100 on the upper support plate 60 is shown in FIGS. 10, 10A. The top cap 20 is further captured by the corresponding complementary shapes of the grip 62 and the lower end 39 of the top cap 20 as the probe holder 100 is lowered into the grip 62 in the upper support plate 60. The probe holder 100 is lowered over the distance between the lower end 39 and the shoulders 23 of the top cap 20 until the probe holder 100 is fully supported on the shoulders 23. The region between the lower end 39 and the shoulders 23 holds and orientates the probe holder 100, retaining it during transport and storage to reduce the chance of inadvertent dislodgement and requiring a user to lift the probe holder 100 to disengage it from the support plate 60. In the particular embodiment shown, two of the first grip 62 for receiving the top cap 20 of a probe holder 100 are illustrated, one of which supports an assembled probe holder 100.

The probe holder 100 may be disassembled for cleaning and disinfection, and the components conveyed and/or stored on the support device. In the embodiments shown in FIGS. 6 and 7, holes 65 in the upper support plate 60 align with supports 55 of the lower support plate 50 to receive separated inner tubes 40 and outer tubes 30. Respective inner tubes 40 and outer tubes 30 rest on a lip 56, and an opening 57 allows for fluid drainage and air circulation, which may facilitate cleaning, disinfection, storage and transport of the holder when not in use.

Apertures 67 in the upper support plate 60 are configured to receive the probe section 110 and the probe electrical connector 108 when not in use, or not contained within the probe holder 100. As an example, a user may place the probe (the probe section 110 and an electrical connector 108) after use in apertures 67 to keep the probe out of the way and prevent damage from falling or impact with equipment. A probe, once used, will proceed to be cleaned and disinfected according to standard procedures in due course, but needs to be protected from damage in the interim. The apertures 67 provide the user with a convenient receptacle on the support for such an application.

The embodiment illustrated in FIG. 6A shows a single hole 58a for receiving the tip 116 of a probe received in the aperture 67a. In this embodiment, a corresponding hole 58b is not shown. In an alternate embodiment, a corresponding hole 58b may be present. Optionally, a tip protector (not shown) may be coupled to the hole 58a and/or 58b in the lower support plate 50 to provide further protection. Such a tip protector may be a tube or sleeve (open or close ended; e.g. a bag or the like) that receives the distal end 114 of the probe when the probe handle 102 rests in aperture 67. In some embodiments a closed ended tube, or sleeve may be useful to contain any matter that drips or drains from the probe after use.

The hole 61 in the upper support plate 60 has a diameter corresponding to dimension F of the bottom cap 10, to receive the bottom cap 10 when inverted, the bottom cap 10 supported in the inverted configuration on the upper support plate 60 by the external circumferential lip 16. The top cap 20 is received in the first grip 62 as described, without clips or inner and outer tubes. In some embodiments, the support device with the probe holder 100 components may then proceed through an automated washing process according to institutional procedures. Alternately, the components of the probe holder 100 may be individually cleaned (manually or in an automated washer or disinfecting process, for example) and set out on the upper and lower supports as described.

Methods and processes for cleaning and/or disinfecting equipment and devices used in medical procedures vary depending on the device or equipment, the particular use of it, limitations imposed by the device—e.g. materials used in its construction, presence or nature of contaminant, and facilities available at the particular institution. Suitable methods of cleaning and/or disinfecting—manual, automated or a combination thereof—will be apparent to those skilled in the art.

Other Embodiments

The present invention has been described with regard to one or more embodiments. However, it will be apparent to persons skilled in the art that a number of variations and modifications can be made without departing from the scope of the invention as defined in the claims. Therefore, although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to," and the word "comprises" has a corresponding meaning. Citation of references herein shall not be construed as an admission that such references are prior art to the present invention. All publications are incorporated herein by reference as if each individual publication was specifically and individually indicated to be incorporated by reference herein and as though fully set forth herein. The invention includes all embodiments and variations substantially as hereinbefore described and with reference to the examples and drawings.

One or more currently preferred embodiments have been described by way of example. It will be apparent to persons skilled in the art that a number of variations and modifications can be made without departing from the scope of the invention.

What is claimed is:

1. A probe holder apparatus comprising;
   a. a removable mechanical retention device;
   b. a first tube comprising a longitudinal slot and two opposing notches at each end of the first tube, the notches configured for engaging the removable mechanical retention device;
   c. a second tube comprising a longitudinal slot, and configured for rotational mating with the first tube; and
   d. a top cap and a bottom cap, each of the top cap and bottom cap configured for releasably engaging the first tube with the removable mechanical retention device, and for restraining rotation of the first tube when so engaged, while permitting rotation of the second tube relative to the first tube between an open configuration and a closed configuration.

2. The apparatus of claim 1, wherein the mechanical retention device is U-shaped 3. The apparatus of claim 2, wherein the U-shaped mechanical retention device comprises two tines, angled away from each other in the same plane.

4. The apparatus of claim 3, wherein the tines are manually compressible for engaging either of the top cap or bottom cap.

5. The apparatus of claim 3, wherein the tines have a rounded end.

6. The apparatus of claim 2, wherein the mechanical retention device is configured for an interference fit.

7. The apparatus of claim 1, wherein the second tube comprises a tag hole at each end to accommodate a status marker.

8. The apparatus of claim 7, wherein the tag hole is substantially opposite the longitudinal slot of the second tube.

9. The apparatus of claim 1, wherein the longitudinal slot of first tube is substantially the same width as the longitudinal slot of the second tube.

10. The apparatus of claim 1, wherein the first tube is longer then the second tube.

11. The apparatus of claim 1, further comprising a tip protector.

12. The apparatus of claim 11, wherein the tip protector has a tapered interior surface.

13. The apparatus of claim 12, wherein tapered interior surface the has one of a unidirectional taper.

14. The apparatus of claim 12, wherein the interior surface is textured.

15. The apparatus of claim 11, wherein an interior surface of the tip protector is a textured surface.

16. The apparatus of claim 1, wherein the top cap comprises a circumferential groove for accommodating a status marker.

17. The apparatus of claim 1, wherein the bottom cap comprises a centre recess for receiving an end of the first tube, a circumferential lip and rotation guide for receiving an end of the second tube.

18. The apparatus of claim 17, wherein the centre recess is of a diameter corresponding to an outer diameter of the second tube.

19. The apparatus of claim 17, wherein the rotation guide is of a diameter corresponding to an outer diameter of the second tube.

20. The apparatus of claim 1, wherein the top cap comprises a neck and interior surface for engaging a probe handle, a circumferential lip an rotation guide for receiving an end of the second tube.

21. The apparatus of claim 20, wherein the rotation guide is of a diameter corresponding to an outer diameter of the second tube.

22. The apparatus of claim 20, wherein the top cap comprises a shoulder for engaging a support plate.

23. The apparatus of claim 22, wherein the top cap comprises an index for directionally engaging a support plate.

24. The apparatus of claim 1, wherein the top cap, bottom cap, first tube, second tube and mechanical retention device are each of monolithic construction.

25. A system for holding a probe comprising the apparatus according to claim 1, and a support structure configured to support the apparatus in a vertical, or substantially vertical, orientation.

26. A support structure configured for supporting the apparatus according to claim 1, comprising:
   a. a first support plate having a mounting portion;
   b. a first grip configured to receive the top cap of the probe holder;
   c. the first grip comprising a lead-in with a width less than an outer diameter of the second tube and an index for directionally engaging the top cap.

27. The support structure of claim 26, wherein the first support plate is fixed to a stationary support.

28. The support structure of claim 27, wherein the stationary support is a shelf, wall or storage cabinet.

29. The support structure of claim 26, wherein the first support plate is fixed to a mobile support.

30. The support structure of claim 29, wherein the mobile support is a vertical support with a wheeled base.

31. The support structure of claim 26, wherein the first support plate further comprises an aperture for receiving a probe.

32. The support structure of claim 26, further comprising a second support plate.

33. The support structure of claim 32, wherein the second support plate comprises a mounting portion, a second grip configured to receive the mated first and second tubes, the second grip aligned with the first grip of the first support plate to maintain the apparatus in a vertical, or substantially vertical configuration; the second grip having a lead-in with a width less then an outer diameter of the second tube.

34. The support structure of claim 33, wherein the first support plate comprises holes, and the second support plate comprises supports for separately receiving the first and second tubes, each of the holes of the first support plate and each of the supports of the second support plate aligned to support the separate first and second tubes in a vertical or substantially vertical configuration. with a width less than an outer diameter of the second tube.

35. The support structure of claim 26, further comprising a hole for separately receiving the bottom cap.

36. The support structure of claim 35, wherein the hole for separately receiving the bottom cap has a diameter F for receiving and supporting the bottom cap in an inverted configuration.

* * * * *